United States Patent [19]

Murib et al.

[11] 3,947,495

[45] Mar. 30, 1976

[54] PROCESS FOR THE PREPARATION OF ACRYLIC AND METHACRYLIC ACIDS

[75] Inventors: Jawad H. Murib; Charles E. Frank; Ben Seeskin, all of Cincinnati, Ohio

[73] Assignee: National Distillers and Chemical Corporation, New York, N.Y.

[22] Filed: July 1, 1974

[21] Appl. No.: 485,047

[52] U.S. Cl............... 260/533 N; 252/428; 252/435
[51] Int. Cl.².......................................... C07C 51/26
[58] Field of Search................................ 260/533 N

[56] References Cited
UNITED STATES PATENTS

| | | | |
|---|---|---|---|
| 2,807,647 | 9/1957 | Cheney et al.................. | 260/604 R |
| 3,009,960 | 11/1961 | Shotts et al..................... | 260/604 R |
| 3,766,265 | 10/1973 | Shiraishi et al................ | 260/530 N |

FOREIGN PATENTS OR APPLICATIONS

| | | | |
|---|---|---|---|
| 971,666 | 9/1964 | United Kingdom............. | 260/533 N |
| 2,162,866 | 8/1972 | Germany........................ | 260/533 N |

*Primary Examiner*—James A. Patten
*Attorney, Agent, or Firm*—Kenneth D. Tremain

[57] ABSTRACT

The selective preparation of acrylic or methacrylic acids by a single step vapor phase oxidation of propylene or isobutylene, respectively, at temperatures up to 300°C. in the presence of a catalyst containing palladium metal and phosphoric acid is improved by the use of a sulfur modifier.

7 Claims, No Drawings

PROCESS FOR THE PREPARATION OF ACRYLIC AND METHACRYLIC ACIDS

BACKGROUND OF THE INVENTION

A number of processes have been proposed for the vapor phase oxidation of propylene or isobutylene to form, inter alia, acrylic acid or methacrylic acid. Such processes are described, for example, in U.S. Pat. Nos. 3,065,264; 3,293,290; 3,392,196; 3,401,198; 3,428,674; and 3,475,488.

One such process which has been developed and utilized for the purpose of acrylic acid, for example, involves a multi-step procedure for the vapor phase oxidation of propylene into acrolein and acrylic acid. The prescribed multi-step operations present obvious processing problems. Moreover, the acrylic acid formed in the successive reaction zones is subject to autooxidation, resulting in relatively low product yields.

In U.S. Pat. No. 3,792,086, an improved process for the preparation of acrylic or methacrylic acids is taught, which involves a vapor phase oxidation of propylene or isobutylene at a temperature of up to 300° C. and in the presence of a catalyst composition containing phosphoric acid and a catalytically effective amount of palladium metal. The acrylic or methacrylic acids are selectively produced in the single-step vapor phase process. Although this process constitutes a very significant advance in the art, it has been found that the continuous operation of the process is often accompanied by a decline of catalyst efficiency due to formation of tar which coats the catalyst preventing efficient contact with the reactants. It has now been found that the use of certain sulfur modifiers unexpectedly results in the retardation of tar formation, an extension of catalyst life and an increase in reaction rate.

Broadly, the use of a sulfur material in an oxidation process is known. For example, U.S. Pat. No. 3,009,960 teaches the oxidation of olefins such as propylene and isobutylene over a copper silicate catalyst in the presence of sulfur to produce unsaturated aldehydes. U.S. Pat. No. 2,590,124 teaches the limited oxidation of gaseous, saturated aliphatic hydrocarbons to produce oxygenated compounds, particularly aldehydes and ketones, using sulfuric acid or sulfur trioxide in the presence of a catalyst. Soviet Pat. No. 336,869 teaches the reduction of transition metal compounds, e.g., of Pd, Cu, Pt and Ru, with sulfur compounds to prepare catalysts which are used in the oxidative addition of hydrogen cyanide to produce the corresponding organonitriles. Many other examples appear in the technical literature. The present vapor phase oxidation of propylene or isobutylene to acrylic or methyacrylic acids is, however, unique and the fact that the sulfur modifiers lead to the retardation of tar formation, extension of catalyst life and increased reaction rates was quite unexpected.

Accordingly, it is the object of this invention to provide a new and improved process for the selective preparation of acrylic and methacrylic acids in substantial conversions. This and other objects and advantages of the invention will become apparent to those skilled in the art from the following detailed description.

SUMMARY OF THE INVENTION

In accordance with the present invention, propylene or isobutylene is oxidized in the vapor phase with molecular oxygen at temperatures of up to 300° C. in the presence of a catalyst composition containing phosphoric acid and a catalytically effective amount of palladium metal, and in the presence of a sulfur modifier, to selectively form the desired acid. The process is carried out at elevated temperatures, employing a heterogeneous catalyst contact system, e.g., a system utilizing a fixed, moving or fluidized catalyst bed. Depending on the nature of the sulfur modifier, it can be added to the catalyst or mixed with the reactants or both. The reactions thus carried out, employing the process of this invention, can be illustrated by the following equations.

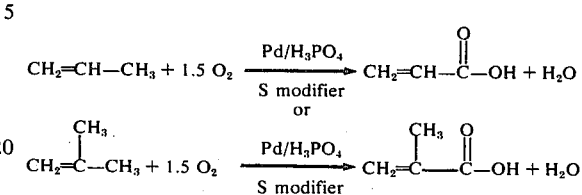

DESCRIPTION OF THE PREFERRED EMBODIMENTS

For convenience, the following description of the preferred forms of the invention will relate principally to the oxidation of propylene to acrylic acid. It will be understood, however, that the instant process is equally applicable to the vapor phase oxidation of isobutylene to methacrylic acid, as set forth hereinabove, and that such latter embodiment is also embraced within the scope of the present invention.

The propylene or isobutylene reacted in the present process can be fed in the pure form or, alternatively, may be impure in the sense that it can contain minor amounts, e.g., up to about 50 mol percent thereof, of a saturated hydrocarbon vapor such as methane, ethane or propane gas. The oxygen feed can similarly be pure oxygen or, alternatively, an oxygen-containing gas mixture such as air or air enriched with oxygen. In addition to these materials, the gaseous feed mixture reacted in the present invention can contain other inert diluents such as carbon dioxide, nitrogen, acetic acid or acrylic acid, as well as other reactive diluents such as acrolein. The gaseous mixture of such reactants is contacted with a catalyst composition of phosphoric acid and a catalytically effective amount of palladium metal, suitably supported on a conventional catalyst carrier such as, for example, silica, alumina, titania, carborundum, carbon, an ion exchange resin, or the like.

The support is impregnated or loaded with phosphoric acid and palladium metal, whether alone or admixed, alloyed or in solid solution with a minor amount of a further metal, e.g., another Group VIII metal, or a Group IB metal such as silver or gold. The palladium metal and phosphoric acid can be deposited on or impregnated in the catalyst carrier in any desired sequence and the resulting supported catalyst composition, however formed, will be active in the vapor phase process. The phosphoric acid can also be added continuously to the reaction mixture in the form of an aqueous solution to maintain a trickle liquid phase over the catalyst bed and in this case, the phosphoric acid in the effluent mixture can be recovered and recycled.

The palladium metal is incorporated in amounts of from about 0.01–5%, preferably from about 0.1–2%, by weight of the total catalyst composition. The phosphoric acid is incorporated in amounts of at least about 1% and up to as much as about 50%, preferably from about 5–30% by weight of the total catalyst composition.

It is necessary that the heterogeneous catalyst contain both palladium metal and phosphoric acid. Other catalyst compositions, such as, for example, palladium metal containing catalyst compositions which do not incorporate phosphoric acid, or catalyst compositions containing noble metals other than palladium either with or without phosphoric acid (e.g., platinum) are not useful in the process. Thus, platinum metal cannot be employed as a catalyst in the vapor phase oxidation of proplylene since the use of such material as a catalyst results in extensive combustion of the olefin to carbon dioxide and water. Similarly, when it is attempted to utilize palladium chloride as the catalyst, halogenation of the olefin occurs as well as some dimerization and trimerization thereof. In contrast, palladium metal-phosphoric acid catalyst compositions provide the highest conversions to, and selectivities of, acrylic or methacrylic acid production.

Palladium metal-phosphoric acid-Group VIII (other than Pd) or Group IB catalyst compositions are similarly active and may exhibit improved stability characteristics as well.

Deposition of the catalytically effective amount of palladium metal utilized in this process can be effected by conventional techniques, such as contacting the catalyst support with a solution of a suitable palladium salt or complex, for example, palladium chloride, palladium acetate, palladium nitrate, or palladium acetylacetonate, and thereafter reducing the palladium compound to the metal with hydrogen or other appropriate reducing agent. Alternatively, the salt may, if desired, be reacted with alkali or alkali metal carbonate to form the corresponding palladium oxide or carbonate and the latter reduced to the catalytically active metal.

When the palladium metal is deposited prior to impregnation of the support with phosphoric acid, the palladium salt may be applied from either aqueus or organic media, i.e., water or organic solvents such as lower alkanols, e.g., methanol or ethanol, benzene, chloroform, or the like. When, on the other hand, the catalytically active palladium metal is deposited on the catalyst support after impregnation of the phosphoric acid, the palladium salt is usually applied from an organic solvent. Organic media is preferred when the palladium is deposited after the phosphoric acid since the presence of water may tend to remove a portion of the phosphoric acid from the carrier.

The catalyst carrier can be loaded with the phosphoric acid by impregnating the support with a phosphoric acid solution, e.g., 40% $H_3PO_4$, and subsequently drying the carrier as, for example, in a vacuum oven. The impregnated support may thereafter be calcined to improve bonding of the phosphoric acid to the carrier.

Commercially available catalyst materials may be utilized in the preparation of the catalyst compositions hereof. For example, either a commercial supported palladium metal catalyst may be treated with phosphoric acid and the sulfur modifier, or a commercial supported phosphoric acid catalyst can have palladium metal and a sulfur modifier deposited thereon, to form catalyst compositions useful herein.

The particular sulfur modifiers found to be useful in this invention include elemental sulfur and certain of its derivatives. Such derivatives include $H_2S$; $SO_2$; $SO_3$; $H_2SO_3$; $H_2SO_4$; thioethers such as thiophene, tetrahydrothiophene and diphenyl sulfide; triphenylsulfonium salts of the formula $(C_6H_5)_3SY$ where Y is Cl, ⅓ $PO_4$, $NO_3$, ½ $SO_4$ or ½ $SO_3$; sulfoxides such as diphenyl sulfoxide and sulfoxides of the formula RR'S=O in which R and R' can each be an alkyl radical of 1–10 carbon atoms; metal sulfides such as $Cu_2S$, CuS and PdS; $CS_2$; and trialkyl thiophosphates of the formulas $(RS)_3P=O$ and $(RS)_3P=S$ in which R is alkyl of 1–10 carbon atoms. It will be recognized by those skilled in the art that some of the sulfur modifiers will be oxidized under the conditions of the instant process. For example, the thioethers are known to oxidize to sulfoxides and sulfones; elemental sulfur oxidizes to $SO_2$ and $SO_3$; $H_2S$ is oxidized to $H_2SO_3$ and $H_2SO_4$; and metal sulfides are oxidized to the corresponding metal sulfites and sulfates. Such oxidation does not, however, interfere with the improvements achieved in the instant invention.

The order in which the palladium metal, phosphoric acid and sulfur modifiers are added to the catalyst support is not critical. Each of these catalyst components can be added before or after the other components or, in some cases, with the other components. The manner in which the sulfur modifier is added to the catalyst is primarily dictated by its physical form and characteristics. For example, if the sulfur modifier is watersoluble, it is convenient to add to it the catalyst in admixture with the aqueous phosphoric acid solution followed by evaporation of the excess water. In those cases where the sulfur modifier is insoluble in water, it is preferably dissolved in a suitable nonaqueous solvent and added to the support prior to impregnation of the catalyst with the phosphoric acid. In the case of gaseous sulfur compounds such as $H_2S$ or $SO_2$, the catalyst may be exposed to the gas at room temperature or, alternatively, the gaseous compound can be admixed with the reaction feed which is fed to the catalyst zone. When the sulfur modifier is a liquid, such as thiophene, it can be vaporized and the vapor similarly added to the reaction feed. Sulfur or sulfur compounds with high volatility can be dissolved in a suitable solvent, e.g., elemental sulfur in $CS_2$, $(C_6H_5)_2S$ in acetone and $(C_6H_5)_3SCl$ in water, impregnated on the catalyst carrier followed by evaporation of the solvent under vacuum or with a stream of air or nitrogen.

The amount of sulfur modifier incorporated into the catalyst composition is not narrowly critical, particularly with respect to the least amount of modifier that can be used. For example, when the modifier is added to the reactant feed, it can be used in amounts ranging from 0.1 to 100 volume parts per million volume parts of reactant feed and when added to the catalyst support, it can be used in amounts as small as 0.003% (as sulfur). In other words, even trace amounts of the sulfur modifier will provide the improved results of the instant invention although, as a practical matter, it is unlikely that the amount of sulfur modifier used will be less than about 0.01 weight percent of the total catalyst and modifier composition. At the other end of the useful range, the sulfur modifier can be employed in amounts as high as about 2% (calculated as S) based on the total catalyst and modifier composition although, as a practical matter, it is unlikely that the modifier will be used in amounts above about 1%.

The reason that the specified sulfur modifiers result in the improved conversion of propylene or isobutylene to acrylic acid or methacrylic acid is not understood. It is hypothesized that the sulfur modifier acts as a scavenger for free radicals that could form through undesirable side reactions thereby retarding tar formation and maintaining clean catalytic active sites. Whatever the actual mechanism, the use of the sulfur modifiers significantly improves the process.

It has been found desirable in accordance with the present invention to additionally incorporate a protonated material, such as water vapor, in the reaction mixture. Whether such material acts as a catalyst promoter or otherwise participates in the complex reaction with the olefin is not presently understood. For coonvenience, the protonated material will hereinafter be referred to as a catalyst promoter although it should be understood that its use in the vapor phase process is contemplated irrespective of the actual mechanism by which it may act.

The water vapor can, e.g., be added to the gaseous feed mixture by bubbling the gaseous olefin and/or oxygen streams through liquid water. Alternatively, the water can be separately vaporized such as by flashing, and metered into the reaction zone. If desired, in lieu of the preferred vapor phase operation of this invention, the water may also be added continuously to the reaction mixture with phosphoric acid to maintain a trickle liquid phase over the catalyst bed.

While stoichiometric proportions of the olefin and oxygen reactants, i.e., 1.5 mols of oxygen per mol of propylene or isobutylene, can be used in the vapor phase process hereof, such compositions are within the flammability range. It is preferred to operate outside the flammability ratios and to use reaction mixtures in which the olefin is the limiting reactant. Generally mixtures are employed in which oxygen is incorporated in amounts of from about 4–45 mol percent in admixture with from about 50–95 mol percent of the olefin, and preferably up to about 60, and desirably 5–40 mol percent of water vapor promoter. Obviously, when inert diluents are present in the reaction mixture as, for example, when oxygen is added in the form of air, the proportions of the several reactants are correspondingly modified. Thus, propylene may be present in amounts of as low as 5 mol percent when the oxygen is introduced as air. In the trickle phase operation, the molar ratio of water to propylene can range between 0.1:1 to 10:1.

The instant vapor phase reaction is carried out at temperatures markedly below those which have generally been regarded as necessary for vapor phase olefin oxidation reactions. It has been previously proposed to conduct such reactions at temperatures of the order of about 350°–400° C. at which levels substantial combustion of the olefin reactant occurs. In accordance with the present invention, selective formation of the desired acids can be obtained at substantially lower temperatures. Thus, the acrylic or methacrylic acids can be obtained at temperatures as low as 50°–200° C. or higher.

The reaction temperature employed in the process varies inversely with the contact time employed, it being possible to use higher reaction temperatures when employing shorter contact times and conversely, lower reaction temperatures at longer contact times. It has thus been found possible to carry out the process of the invention at temperatures of as high as 300° C. using relatively short contact times.

The oxidation process is conducted either at atmospheric or elevated pressures, the use of higher pressures increasing product conversion. The reaction can thus be effected at pressures of up to about 300 psi. It is generally preferred, however, to carry out the vapor phase process under pressures only slightly in excess of atmospheric, e.g., up to about 100 psi, to increase productivity and catalyst efficiency.

After the gaseous reaction mixture contacts the catalyst composition, the exhaust gases are cooled and scrubbed to facilitate recovery of the acrylic or methacrylic acid. The desired material may then be separated by any convenient means such as distillation. Unreacted feed material separated from the recovery of effluent mixture can then be recovered and recycled for further reaction.

The following Examples are presented in order to further illustrate the invention but are not intended to limit it. Throughout this specification and claims, all parts and percentages are by weight and all temperatures are in degrees centigrade unless otherwise specified. Further, as employed herein, the conversion to acrylic or methacrylic acid, and the selectivities of formation of such products are defined as follows:

$$\% \text{ Conversion} = 100 \times \frac{\text{number of mols of olefin converted}}{\text{number of mols of olefin fed}}$$

$$\% \text{ Selectivity} = 100 \times \frac{\text{number of mols of product}}{\text{number of mols of olefin reacted.}}$$

In those Examples in which the sulfur modifier is added to the catalyst support, the proportions of palladium metal, phosphoric acid and modifier are given as percentages of the total weight of the catalyst, i.e., Pd, $H_3PO_4$, sulfur modifier and support. In those Examples where the sulfur modifier is added to the reactant feed, the proportions of palladium metal and phosphoric acid in the catalyst are given as percentages of the total weight of the palladium metal, phosphoric acid and the support.

EXAMPLE 1

A pyrex glass reactor, 12 cm × 2.5 cm outer diameter provided with thermowells (0.8 cm outer diameter) was packed with 30 ml (bulk volume) of a surface-coated catalyst containing 1% Pd, 2% Au and 16% $H_3PO_4$ supported on ⅛ inch diameter extruded silica (hereinafter designated catalyst A). An identical reactor was similarly packed with the same catalyst which also contained 8% triphenylsulfonium chloride (hereinafter designated catalyst B). Catalysts A and B were heated in an oil bath at 180° C. A stream of mixed vapors having a ratio $C_3H_6:O_2:N_2:H_2O$ of 1:2:7:8:5 was split and passed through each of the heated catalyst beds at a rate such that the contact time was 3.5 seconds. The reaction mixtures were than bubbled separately through water held at 0° C. Analysis of the aqueous solutions collected during 1 hour intervals by gas chromatography and acid titration gave results which are set forth in Table I.

Catalyst B, after an induction period of 50 hours, produced acrylic acid at the rate of about 40 g/l.cat./hr with essentially no decline in activity during 213 hours of continuous operation. Catalyst A gave an initial production of 33.8 g/l.cat/hr and then lost 26% of its initial activity during the 213 hours. In the case of catalyst B, conversion remained essentially the same (40% based on the propylene feed) while that of catalyst A lost 23.3% of its initial value.

At the end of the 213th hour, the ratio of oxygen to propylene in the reactant feed was increased from 2:1 to 3:1. Analysis of the resulting aqueous solutions are also shown in Table I. The productivity of catalyst B rose to 52.3 g/l.cat/hr compared to 30.6 g/l.cat/hr obtained without the triphenylsulfonium chloride. Thus, the increase in production rate corresponded to a promotion of 71%. Examination of the cross-section of the pellets of catalyst B after 285 hours of operation showed that the interior remained white while the interior of catalyst A was black due to tar and polymer formation.

The results obtained at the end of 197 hours using an oil bath at 195° C. are shown in Table II.

TABLE II

| Catalyst | Temp. °C Reactor | Acrylic Acid g/l.cat/hr | % Conv. | % Sel. |
|---|---|---|---|---|
| D (no sulfur modifier) | 203 | 33.8 | 53.6 | 75.8 |
| E $(C_6H_5)_2S$ | 214 | 39.4 | 60.0 | 79.2 |

Table II shows use of the diphenylsulfide resulted in a 16.6% increase in the reaction rate.

TABLE I

| | CATALYST A - NO SULFUR MODIFIER | | | | | CATALYST B - $(C_6H_5)_3SCl$ | | | | |
|---|---|---|---|---|---|---|---|---|---|---|
| Time Hours | Temp. °C Bath | Reactor | g/l.cat/hr | Acrylic Acid % Conv. | % Sel. | Temp. °C Bath | Reactor | g/l.cat/hr | Acrylic Acid % Conv. | % Sel. |
| 23 | 172 | 186 | 33.8 | | | 172 | 180 | 5.3 | | |
| 31 | 180 | 194 | 32.3 | | | 176 | 197 | 15.0 | | |
| 50 | 180 | 194 | 31.5 | 33 | 73.5 | 180 | 207 | 38.2 | 40 | 73.8 |
| 74 | 180 | 193 | 26.2 | 28.2 | 71.7 | 180 | 207 | 37.2 | 38.2 | 75.2 |
| 99 | 180 | 192 | 26.4 | 28.3 | 71.9 | 180 | 207 | 44.0 | 43.5 | 78.1 |
| 193 | 180 | 193 | 26.2 | 26.4 | 76.7 | 180 | 207 | 40.0 | 39.1 | 81.0 |
| 213 | 180 | 193 | 24.9 | 25.3 | 72.7 | 180 | 207 | 39.5 | 39.1 | 78.0 |
| | | | | | $C_3:O_2:N_2:H_2O = 1:3:6:8.5$ | | | | | |
| 238 | 175 | 189 | 28.6 | 28.7 | 77.3 | 175 | 208 | 47.3 | 48 | 76.6 |
| 261 | 174 | 188 | 30.6 | 31.2 | 75.8 | 174 | 208 | 52.3 | 50.1 | 79.7 |

EXAMPLE 2

A catalyst C was prepared containing 1% Pd, 2% Au, 16% $H_3PO_4$ and 2.5% triphenylsulfonium dihydrogen phosphate. Following the procedure of Example 1, side-by-side reactions were carried out using a propylene:oxygen:nitrogen:water vapor ratio of 1:3:6:8.5. At the end of 196 hours of operation at 1 atmosphere, 221° C. and 3.5 seconds contact time, catalyst C produced acrylic acid at the rate of 53.8 g/l.cat/hr in contrast to 38.4 g obtained with catalyst A (no sulfur modifier). Thus, the use of the sulfonium compound gave an increase of 56% in the reaction rate.

EXAMPLE 3

Two catalysts were prepared. Catalyst D contained 0.7% Pd, 1.36% Au and 33% $H_3PO_4$ supported on activated granular carbon. Catalyst E contained 0.7% Pd, 1.36% Au, 33% $H_3PO_4$ and 0.17% diphenylsulfide supported on activated granular carbon. Following the procedure of Example 1, acrylic acid was produced from a reactant feed containing 2.8% propylene, 10.8% oxygen, 39.4% nitrogen and 47% water vapor, at 1 atmosphere pressure and a contact time of 2.1 seconds.

EXAMPLE 4

The procedure of Example 1 was repeated in two side-by-side reactors both containing a catalyst F which had 1.25% Pd, 2.4% Au and 15% $H_3PO_4$ supported on silica. The reactor feed consisted of 5.4% propylene, 16.1% oxygen, 32.4% nitrogen and 46.1% water vapor. A single dose of 20 cc $H_2S$ (measured at amospheric conditions) was initially added to one of the reactor feeds and passed through the catalyst bed at 186° C. The results obtained at atmospheric pressure and a contact time of 2.6 seconds are given in Table III.

TABLE III

| Sulfur Modifier | Temp. °C Bath | Reactor | Operating Time, Hrs. | Acrylic Acid g/l.cat/hr | % Conv. | % Sel. |
|---|---|---|---|---|---|---|
| None | 186 | 222 | 200 | 34.8 | 43.1 | 71.0 |
| $H_2S$ | 186 | 223 | 200 | 53.5 | 54.0 | 76.2 |

Table III demonstrates that the use of the hydrogen sulfide resulted in an increase in the reaction rate of 53.8%.

EXAMPLE 5

The procedure of Example 4 was repeated except that the 20 cc dose of $H_2S$ was replaced with a 20 mg dose of thiophene vapor. The results are shown in Table IV.

TABLE IV

| Sulfur Modifier | Temp. °C Bath | Reactor | Hours on Stream | Acrylic Acid g/l.cat/hr | % Conv. | % Sel. |
|---|---|---|---|---|---|---|
| None | 186 | 218 | 31 | 31.6 | 43.1 | 71.0 |
| Thiophene | 186 | 212 | 31 | 48.2 | 56.2 | 70.5 |

The use of the thiophene increased the reaction rate by 52.5%.

EXAMPLE 6

The procedure of Example 4 was repeated to compare catalysts F and G. Catalyst G contained 1.23% palladium, 2.4% Au, 0.03% palladium sulfide and 15% phosphoric acid supported on silica. The results are shown in Table V.

TABLE V

| Catalyst | Temp.°C Bath | Temp.°C Reactor | Operating Time, Hrs. | Acrylic Acid g/l.cat/hr |
|---|---|---|---|---|
| F (no sulfur modifier) | 196 | 220 | 120 | 42.3 |
| G (PdS) | 196 | 226 | 120 | 59.1 |

The use of PdS increased the rate of acrylic acid production by 40%.

EXAMPLE 7

The procedure of Example 4 was repeated using catalysts H and I. Catalyst H contained 1.24% Pd., 2.4% Au and 15% $H_3PO_4$ supported on silica. Catalyst I contained 1.24% Pd, 2.4% Au, 0.2% elemental sulfur and 15% $H_3PO_4$ supported on silica. The elemental sulfur was deposited on the catalyst from a carbon disulfide solution followed by evaporation of the solvent. The results are shown in Table VI.

TABLE VI

| Catalyst | Temp. °C Bath | Temp. °C Reactor | Operating Time, Hrs. | Acrylic Acid g/l.cat/hr |
|---|---|---|---|---|
| H (no sulfur modifier) | 196 | 220 | 120 | 42.3 |
| I (S°) | 196 | 217 | 120 | 47.0 |

The use of sulfur gave an 11% higher production rate.

EXAMPLE 8

Propylene was converted into acrylic acid at a temperature of 188°–209°C., a contact time of 3.5 seconds and a reactant feed in which the ratio of $C_3H_6:O_2:N_2:H_2O$ was 1:3:6:8.5. Various catalyst components supported on silica extrudates (183 m²/g) were utilized. The particular catalysts employed and the resulting acrylic acid production are shown in Table VII.

TABLE VII

| Catalyst Component | Acrylic Acid g/l.cat/hr |
|---|---|
| Pd | trace |
| $H_3PO_4$ | none |
| $(C_6H_5)_3SCl$ | none |
| $H_3PO_4$—$(C_6H_5)_3SCl$ | none |
| Pd—$(C_6H_5)_3SCl$ | 1.1 |
| Pd—$H_3PO_4$—$(C_6H_5)_3SCl$ | 27.6 |

EXAMPLE 9

Production of Methacrylic Acid

The procedure of Example 2 was repeated except that isobutylene was used instead of propylene. In two side-by-side reactors catalysts, J and K, both containing 1.1% Pd and 2.1% Au and 26% $H_3PO_4$, were used. To catalyst K was additionally added 0.72 g of $(C_6H_5)_3SH_2PO_4$. The results are given in Table VIII.

TABLE VIII

| Catalyst | Temp.°C Bath | Temp.°C Reactor | Operating Time, Hrs. | Methacrylic Acid g/l.cat./hr |
|---|---|---|---|---|
| J (no sulfur modifier) | 189 | 212 | 47 | 3.1 |
| K ($\phi_3SH_2PO_4$) | 189 | 203 | 47 | 6.6 |

Reactor J gave acrylic acid as the major product with methacrylic, acetic and propionic acids as by-products. Reactor K, however, gave methacrylic acid as the major product with minor amounts of propionic and acetic acids and none or trace amounts of acrylic acid.

The use of $(C_6H_5)_3SH_2PO_4$ gave a more than two-fold increase in the rate of methacrylic production with retardation of acrylic acid formation.

Various changes and modifications can be made in the process and catalysts of this invention without departing from the spirit and the scope thereof. The various embodiments set forth herein were for the purpose of further illustrating the invention but were not intended to limit it.

We claim:

1. In a process for the preparation of acrylic or methacrylic acid by oxidizing propylene or isobutylene in the vapor phase with molecular oxygen in the presence of a catalyst composition consisting of phosphoric acid and a catalytically effective amount of palladium metal the improvement which comprises conducting the process in the presence of a sulfur catalyst modifier selected from the group consisting of elemental sulfur, $H_2S$, $SO_2$, $SO_3$, $H_2SO_3$, $H_2SO_4$, thioether, triphenylsulfonium salt of the formula $(C_6H_5)_3SY$ where Y is Cl, ⅓ $PO_4$, $NO_3$, ½ $SO_4$ or ½ $SO_3$, diphenyl sulfoxide, dialkyl sulfoxide, metal sulfide, trialkyl thiophosphate of the formulae $(RS)_3P=O$ and $(RS)_3P=S$ wherein R is alkyl of 1–10 carbon atoms, and $CS_2$.

2. The process of claim 1 wherein the catalyst composition is a supported catalyst material having phosphoric acid impregnated therein, and a catalytically effective amount of a material selected from palladium metal or an alloy, mixture or solid solution of palladium metal with a Group IB or Group VIII metal deposited thereon.

3. The process of claim 2 wherein said thioether is thiophene, tetrahydrothiophene, or diphenyl sulfide, said dialkyl sulfoxide is of the formula RR′S=O in which R and R′ are each alkyl of 1–10 carbon atoms, and wherein said metal sulfide is $Cu_2S$, CuS, PdS or Pd$_2$S.

4. The process of claim 2 wherein said catalyst composition contains from 0.01–5% by weight palladium metal and from 1–50% by weight phosphoric acid and wherein the reaction is carried out at temperatures of up to 300° C. and under pressures of up to 300 psi.

5. The process of claim 1 wherein the respective materials are reacted in proportions of from 5–95 mol percent of propylene or isobutylene with from 5–45 mol percent of oxygen and wherein the gaseous reaction mixture further includes water vapor in an amount of up to 60 mol percent thereof.

6. The process of claim 2 wherein said sulfur modifier is added to said supported catalyst before the reaction mixture is contacted with the catalyst.

7. The process of claim 2 wherein said sulfur modifier is added to the gaseous reaction mixture contacted with the supported catalyst.

* * * * *